United States Patent [19]

Olsson et al.

[11] Patent Number: 5,614,218
[45] Date of Patent: Mar. 25, 1997

[54] CONTROLLED RELEASE PREPARATION

[75] Inventors: Birgitta Olsson, Stenhamra; Maritta A. Pesonen, Skärholmen; Gert Ragnarsson, Bro, all of Sweden

[73] Assignee: Pharmacia & Upjohn Aktiebolag, Stockholm, Sweden

[21] Appl. No.: 213,518

[22] Filed: Mar. 16, 1994

[30] Foreign Application Priority Data

Mar. 30, 1993 [SE] Sweden .................... 9301057

[51] Int. Cl.$^6$ .................... A61K 9/48
[52] U.S. Cl. .................... 424/456; 424/457; 424/458; 424/459; 424/463; 424/474; 424/475; 424/489
[58] Field of Search .................... 424/456, 457, 424/458, 459, 463, 474, 475, 489

[56] References Cited

FOREIGN PATENT DOCUMENTS

| 0080341 | 6/1983 | European Pat. Off. . |
| 0097523 | 1/1984 | European Pat. Off. . |
| 0377518 | 7/1990 | European Pat. Off. . |
| 921366 | 2/1992 | South Africa . |
| 91/01722 | 2/1991 | WIPO . |
| 94/03161 | 2/1994 | WIPO . |

OTHER PUBLICATIONS

Hardy, Colonic Transit and Drug Delivery, Drug Delivery to the Gastrointestinal Tract, Ellis Horwood Limited, Halsted Press, pp. 75–81.
Olsson, et al., Bioavailability and Gastro–Intestinal Transit of Two Morphine CR Tablets, Proceed. Intern. Symp. Control. Rel. Bioact. Mater., 18(1991), Controlled Release Society, Inc., pp. 433–434.

Primary Examiner—Thurman K. Page
Assistant Examiner—Raj Bawa
Attorney, Agent, or Firm—Pollock, Vande Sande & Priddy

[57] ABSTRACT

An oral controlled release pharmaceutical preparation in the form of a tablet, capsule or sachet containing a plurality of coated particles comprising a therapeutically effective amount of a salt of morphine coated with a barrier membrane providing a controlled, preferably pH-independent, release of morphine in that the serum concentration of morphine obtained is at least 50% of the maximum serum concentration during at least 12 hours after administration of a single dose, and providing a significantly reduced plasma concentration fluctuation compared to known morphine preparations. A method for the manufacture of such a preparation and the use of such preparations for the manufacture of an analgesic useful in the treatment of severe chronicle pain are also provided.

13 Claims, 1 Drawing Sheet

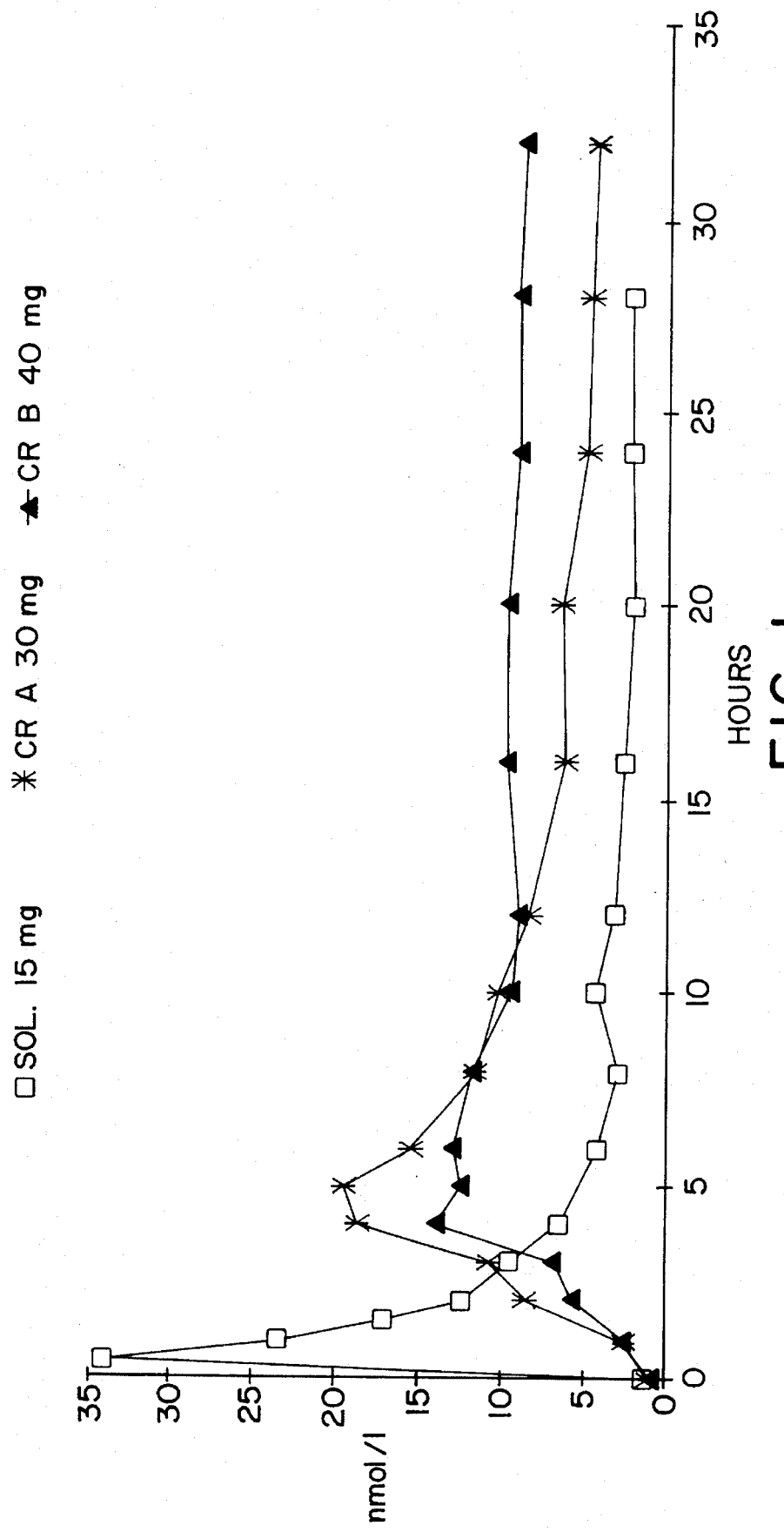

CONTROLLED RELEASE PREPARATION

FIELD OF INVENTION

The present invention relates to a new pharmaceutical preparation containing a number of coated particles comprising a salt of morphine coated with a barrier membrane with a controlled release of morphine over the main part of the dose interval when administered once daily, providing a significantly reduced plasma concentration fluctuation compared to known morphine preparations. The invention is also related to a method for the manufacture of such a preparation and the use of such preparations for the manufacture of an analgesic useful in the treatment of severe chronical pain.

BACKGROUND OF THE INVENTION

Morphine has a serum haft-life of 2–4 hours and the duration of its analgesic effect is about 4–6 hours after oral administration. The short duration makes it necessary to administer morphine orally 4–6 times daily to achieve a satisfactory analgesic effect. This has led to a development of various oral controlled release formulations of morphine. Oral controlled release products containing morphine on the market e.g. MST Continus® or MS Contin® and Dolcontin®, are in general administered 2–3 times a day in order to give a sufficient pain relief over the entire dosage interval. Conventional matrix tablets consisting of morphine and an inert carrier composition are characterized by a fast initial drug release leading to an early peak of morphine plasma concentration followed by a decrease in release, which will be especially pronounced in the lower intestinal system where more neutral or weakly basic conditions prevail. There has been a demand to find a way to obtain an oral drug preparation having a more even release of morphine in order to get smoother blood concentration and effect profiles over the entire dosage interval when administered once daily.

EP-B-0 097 523 discloses such a preparation where the drug is distributed in a controlled release matrix partly in the form of a salt and partly as a free base. This preparation increases dissolution time and biovailabilty without the need of applied coating membranes.

It is known that morphine gives considerable problems in the development of matrix tablets which have been considered to be due to poor absorption properties of morphine in the distal parts of the gastrointestinal tract, see Proceed. Intern. Syrup. Control. Rel. Bioact. Mater., 18, 1991, pag. 433–434, (B. Olsson et al).

There are several examples of formulations which are designed to overcome the drawbacks of oral matrix tablets by providing a constant or controlled release rate over a more extended period. An example of such formulations is multiple unit (MU) formulations as disclosed previously in EP-A-0 080 341 and in WO-A-91/01722.

The depot preparation consisting of a large number of small units is considered to promote good absorption properties by being dispersed over a large area in the gastrointestinal tract and having a lower transit rate especially in the colon, compared to matrix tablets, see Drug Delivery to the Gastrointestinal Tract, Ed. By J G Hardy Et. al., Chichester, Ellis Howard Ltd, 1989, pages 75–81: "Colonic transit rate and drug delivery". In addition multiple unit formulations are preferable to one single unit as they may be divided into smaller portions all having the same release and absorption properties which will give greater flexibility in selection of the size of the dose, will facilitate administration of the drug to patients having problems to swallow and will considerably reduce the risk of dose dumping.

Also in EP-A-0 377 518 there is described a sustained release pellet formulation, but with core elements which may comprise the salt of a morphine compound coated with a hybrid coating admitting a slow release at an acidic pH and relatively constant higher release at a less acidic to basic pH. The preparations according to EP-A-0 377 518 exhibit a limited bioavallibility, restricting the administration to at least twice daily.

ZA-A-921366 relates to a solid controlled release dosage form for improved storage stability at elevated temperature and/or elevated relative hunidity. The controlled release is obtained by overcoating a substrate including a therapeutically active ingredient with a coating derived from an aqueous dispersion of ethylcellulose and then curing the coated substrate at an elevated relative humidity and at a temperature above the glass transition temperature for the coating. There is no indication in ZA-A-921366 that any of the preparations would be suitable for a once daily administration.

DESCRIPTION OF THE INVENTION

The object of the present invention is to provide a once-daily preparation of morphine i.e. a preparation with an even blood concentration profile when the preparation is administered once daily, without any substantial loss in bioavallability. The preparation should preferably also have a release rate of morphine which is substantially independent of its position in the gastrointestinal tract. Such a preparation represents an improvement in the treatment of severe opioid sensitive pain and supplies a convenient oral dosage form which gives an even effect and reduced risk of pain breakthrough.

The present invention is related to a multiple unit preparation of morphine consisting of small particles of morphine salts and a coated barrier layer which preferably provides a pH independent release, methods for their manufacture and the use of such preparations for the treatment of severe opioid sensitive pain by a once daily administration.

In general, a multiple unit preparation contains of at least 50, and suitably of at least 150, individual drug including particles, e.g. crystals, beads or pellets. A multiple unit preparation in accordance with the present invention has a controlled rate of drug release during 15–24 hours for all possible strengths of the preparation in the preferred interval of 10–400 mg morphine (salt). However, higher total dosages of morphine are conceivable in certain applications and those will also be possible to administer with the multiple unit preparation according to the present invention. This means that a multiple unit preparation to fulfil the criteria of the invention shall give serum concentrations greater than or equivalent to 50% of the maximum concentration during at least 12 hours, suitably for at least 18 hours and preferably for at least 24 hours. A multiple unit preparation according to the present invention should suitably give a serum concentration greater than or equivalent to 40% of the maximum concentration during at least 18 hours, and preferably for at least 24 hours. This means that the preparations of the present invention can be advantageoulsy used for dosage intervals up to 24 hours, most preferably for once-daily administration, less preferably for twice-daily administration.

Other objects of the present invention are low peak plasma concentration of morphine, release of 50% of the total dose within 4–10 hours and more than about 80%, preferably more than 90%, bioavailability of the preparation when compared to traditional preparations as instant release tablets and oral solutions.

It has been found that these demands are met surprisingly well by a preparation containing a large number of small particles comprising a salt of morphine which are coated with a barrier layer containing at least one component insoluble in the fluids of the gastrointestinal system to provide high serum concentrations for a prolonged period of time.

The particles contain a salt of morphine and optionally pharmaceutically acceptable excipients such as lactose and microcrystalline cellulose and have a size of 0.2 to 3 mm, preferably 0.7 to 1.4 mm. Suitable salts of morphine are soluble salts, such as morphine hydrochloride, morphine sulphate, and salts of certain organic carboxylic acids. The particles are prepared with conventional methods such as mixing and granulation of the morphine salt with the excipient or excipients, extrusion, spheronization, drying and sieving the particles to an acceptable size range.

Examples of suitable barrier coating materials which are substantially insoluble in the fluids of the gastrointestinal tract are natural and synthetic polymers such as ethyl cellulose, Eudragit RS, polyvinyl chloride, natural or synthetic waxes as carnauba wax. Ethyl cellulose is an especially suitable insoluble material which is available in different grades and in special qualities for aqueous based barrier coatings. According to the invention it is preferable to use ethyl cellulose having a viscosity of 5 to 15 cps, but also other types of cellulose may be used.

In a barrier coating preferred according to the present invention, the water insoluble component or components will be mixed with one or several components soluble in water. Suitable water soluble components are polymers like hydroxypropyimethyl cellulose, hydroxypropyl cellulose, Eudragit RL and Eudragit NE. Instead of water soluble polymers other water soluble substances as sugar, lactose and different salts can be used in the formation of a partly erodable film with a pH-independent release rate. Eudragit is the trade name of a substance useful for film coating of controlled release particles, which can be both soluble and insoluble in the fluids of the gastro intestinal tract (see above). Eudragit RL and RS (Röhm Pharma) are copolymers synthesised from acrylic and methacrylic esters with a low content of quaternary ammonium groups. Euciragit RL and RS differ in the molar ratios of the ammonium groups to the remaining neutral (meth)acrylic add esters (1:20 and 1:40 respectively). Eudragit NE is the aqueous dispersion of a neutral copolymer based on ethyl acrylate and methyl methacrylate. These above mentioned properties result in different permeability characteristics.

The coating procedure can be performed by conventional means such as a spraying equipment, a fluidised bed and equipment for drying and size fractionating. The liquid used in the coating procedure contains one or several barrier layer forming components and one or several solvents, such as ethanol, acetone, methyl isobutyl ketone (MIBK), water and others well known in this technical field. The coating liquid can be in the form of a solution, a dispersion, an emulsion or a melt, depending on the specific nature of the coating constituents.

Plasticizers and pigments may optionally be used to modify the technical properties or change the permeability of the coating. The coating membrane is made of one or more polymers and has preferably a virtually pH independent permeability properties within the pH range of 1.0 to 7.0. At higher pH a reduction in the release of morphine may be observed but this is not due to the properties of the polymeric layer but depends on the reduced solubility of morphine salts at high pH values.

A characteristic and suitable coating composition within the scope of invention consists of ethyl cellulose and hydroxypropylmethyl cellulose and a certain amount of triethyl citrate as plasticizer. A specific example of the coating composition is ethyl cellulose and hydroxypropylmethyl cellulose in relations from 55/35% to 80/10% w/w with 10% triethyl titrate as a plasticizer.

Each coated morphine particle represents an individual controlled release unit, releasing the drug at a predetermined rate preferably independent of its position in the gastrointestinal tract. Coated pellets according to the invention can be used in different types of dosage forms such as gelatine capsules, compressed tablets or sachets.

The invention makes it possible to obtain a dosage form of morphine salts that can be given once daily and still produce almost constant plasma concentrations of the drug and a high biological availability.

BRIEF DESCRIPTION OF THE DRAWING

FIG. 1 is a graph showing mean serum concentrations in tested individuals versus time.

DETAILED DESCRIPTION OF THE INVENTION

The following examples are intended to illustrate suitable preparations within the scope of invention, which meet the demands set on the oral morphine formulations in the previous text. The examples shall not be regarded as limiting for the scope of invention and alterations and modifications of parameters and ingredients can be made without departing from the context of the present invention.

EXAMPLE 1

Manufacturing of morphine pellets

Morphine hydrochloride pellets to be used in a controlled release preparation according to the present invention can be manufactured by the following measures.

Morphine hydrochloride was selected as a suitable salt for the formulation work. It has very similar properties to the most common alternative morphine sulphate, regarding e.g. water solubility. Further studies showed that the solubility is not critically dependent on the pH-value of the dissolution medium (within the physiological range). This is in accordance with its high pKa-value (7.5). Microcrystalline cellulose is a common diluent in pellet formulations as it gives very good technical properties. Lactose is used as a soluble constituent.

1. Mixing and granulating: Morphine hydrochloride (40% w/w), lactose (40% w/w) and microcrystalline cellulose (Avicel PH-101) (20% w/w) totally 1500 gram were dry-mixed in a planetary type mixer (Kenwood Major) at a low mixing speed (speed adjustment <1) for 10 minutes. Water (585 gram) was added and the mass was granu-lated for 5 minutes at speed adjustment 2.

2. Extrusion: Extrusion was performed in a NICA E-140 extruder (Lejus Medical AB, Sweden) through a perforated screen with drilled orifices of 1.0 mm diameter. The speed of the agitator and the feeder were set on the lowest values.

3. Spheronization: Spheronization was conducted in a marumerizer (Ferro Mecano AB, Sweden). The speed of the marumerizer plate was adjusted to 450 rpm. The number of spheronization rounds were 5, with about 400 grams of wet extrudates on the plates at each run.

4. Drying: Drying was performed in a fluid bed dryer (Aeromatic AG West Germany) at an IN-temperature of 50° C. The batch was divided into sub-batches of 600–700 grams wet particulate cores. Each sub-batch was dried for 5 minutes at the air velocity adjustment 20 in order to obtain individual cores rather than aggregates. The sub-batches were then mixed and the whole batch was dried at adjustment 12 for 65 minutes. The end OUT-temperature was 36° C. The yield of dry cores after drying was 1437 gram and 96% w/w.

5. Sieving: Sieving was performed by using analytical sieves with sieve sizes of 0.71 mm and 1.40 mm, respectively. The yield of dry cores after sieving was 1337 gram and 89% w/w.

The yields were 96 and 89% w/w after drying and sieving, respectively. The mass was lost during the extrudation and sieving procedures. A sieving analysis before and after abrasion of the cores showed that about 93% of the cores had a size between 0.71 and 1.0 mm. A crushing strength analysis showed that the mean crushing strength of 1.0 mm particles was 4.71N. A hardness value at this level makes it possible to coat the particles in a small as well as in a larger equipment. The obtained morphine hydrochloride cores are well suitable for production in large scale.

EXAMPLE 2

Coating of morphine hydrochloride pellets

Morphine hydrochloride cores manufactured in accordance with Example 1 can be coated with controlled release membranes to prepare multiple unit formulations within the scope of the present invention.

Hydroxypropylmethyl cellulose (HPMC) E5 and ethyl cellulose (EC) 10 cps were used as film formers together with triethyl citrate (TEC) as a plasticizer. The coating solution contained 99.5% ethanol and methyl isobutyl ketone (MIBK).

The coating was performed using a spray coating equipment (NICA FB-coater, Sweden). The spray gun used was a Binks & Bullows with a J92R liquid nozzle and a J930 air nozzle. A net device was placed in the top of the fluidised bed to avoid loss of cores to the cyclone output. The spray gun was mounted on a height over the bottom of the bed of 185 min. Ethanol/MIBK mixture was pumped through the system prior to the start of the coating, and there was consequently liquid present between the pump housing and the spray gun. The morphine hydrochloride cores prepared as in Example 1 were loaded. The cores were pre-heated at 55° C. with an air velocity of 20–25 m³/h for 4 minutes: At the start of the coating, the bed temperature was 32°–36° C. The coating was started using the following process parameters: atomising pressure 500 kPa, air velocity 85 m³/h and a solution flow of about 24 ml/min. The registered IN-temperature varied between 53° and 56° C., the OUT-temperature between 34° and 38° C. during the coating.

Morphine hydrochloride cores from the same batch were coated with different proportions of EC/HPMC in the film coating solution. Different amounts of the polymer solution was also tested in order to obtain a suitable in-vitro dissolution rate at a suitable film thickness (too thin a film may give reproducibility problems), see Table 1 below. A mixture of 5.5 parts of EC and 3.5 parts of HPMC was selected and an amount of approximately 8 mg of coating material per capsule content (approximately 7.5%w/w per dose) was found to be suitable.

It is well known, however, that the amount of polymer will vary considerably with rather small variations in the mean pellet size (or surface area), which means that a careful optimisation must be done for each produced pellet quality to ensure an adequate dissolution rate.

The coated spheres were sieved through a 1.4 mm sieve and spheres with a size less than 1.4 mm are collected. The collected spheres were filled into hard gelatine capsules (Hard gelatine capsule, colour white, No. 2) with a normal weight of 0.17 g (net weight 108 mg). The capsules meet the requirements of the mass uniformity test in Ph. Eur. The mean content of active component in the capsules are between 36 and 44 mg.

The composition per capsule was:

| | |
|---|---|
| Morphine hydrochloride | 40 mg |
| Lactose | 40 mg |
| Microcrystalline cellulose | 20 mg |
| Water (purified), evaporated during the process | q.s. |
| Ethyl cellulose (EC) | 3.5–5.3 mg |
| Hydroxypropyl methylcellulose (HPMC) | 2.2–3.4 mg |
| Triethyl citrate (TC) | 0.6–1.0 mg |
| Ethanol 99.5% (evaporated) | q.s. |
| Methyl isobutylketone (evaporated) | q.s. |
| Hard gelatine capsule, white, No. 2 | approx. 60 mg |

The film components are selected to give release properties that are virtually independent of pH and agitation. At very high pH-values, the release rate is reduced as expected when considering the pKa-value of morphine hydrochloride (see Tables 2 and 5). The agitation speed had no significant effect on the release rate (see Tables 2 and 6)

The in-vitro dissolution test is carried out with the USP dissolution apparatus No. II (paddle) at 50 rpm, 37° C., in a phosphate buffer solution, pH 6.8. Six individual capsules are tested.

The amount released (% of labelled amount) is calculated:

| | |
|---|---|
| <15% released after | 1 h |
| 35–65% released after | 6 h |
| 55–80% released after | 12 h |
| not less than 80% released after | 24 h |

TABLE 1

In vitro dissolution rate. Morphine hydrochloride pellets according to above, but with different amounts and proportions of polymers in the coating.
Method: USP dissolution apparatus No. II (paddle) at 50 rpm, 37° C., in a phosphate buffer solution, pH 6.8.

| Amount of film (% w/w) | 1.4 | 2.7 | 8.0 | 2.7 |
|---|---|---|---|---|
| Prop:EC:HPMC:TEC | 8:1:1 | 8:1:1 | 8:1:1 | 7:2:1 |
| Time (hours) | percent dissolved morphine hydrochloride, n = 2 | | | |
| 1 | 45 | 17 | 5 | 26 |
| 2 | 75 | 30 | 9 | 47 |
| 3 | 91 | 40 | 14 | 64 |
| 4 | 98 | 51 | 17 | 76 |
| 5 | 101 | 59 | 21 | 85 |
| 6 | 104 | 65 | 25 | 90 |
| 7 | 105 | 71 | 28 | 93 |
| 8 | 106 | 74 | 31 | 95 |

TABLE 1-continued

In vitro dissolution rate. Morphine hydrochloride pellets according to above, but with different amounts and proportions of polymers in the coating.
Method: USP dissolution apparatus No. II (paddle) at 50 rpm, 37° C., in a phosphate buffer solution, pH 6.8.

| | | | | |
|---|---|---|---|---|
| 10 | — | — | — | — |
| 12 | — | — | — | — |
| 24 | 106 | 97 | 64 | 102 |

| Amount of file (% w/w) | 4.2 | 4.6* | 7.5* |
|---|---|---|---|
| Prop:EC:HPMC:TEC | 7:2:1 | 5.5:3.5:1 | 5.5:3.5:1 |
| Time (hours) | percent dissolved morphine hydrochloride, n = 2 | | |
| 1 | 16 | 16 | 8 |
| 2 | 29 | 32 | 17 |
| 3 | 40 | 48 | 26 |
| 4 | 51 | 60 | 34 |
| 5 | 60 | 69 | 42 |
| 6 | 67 | 78 | 49 |
| 7 | 72 | 83 | 55 |
| 8 | 76 | 87 | 60 |
| 10 | — | 92 | 70 |
| 12 | — | 96 | 74 |
| 24 | 100 | 99 | 93 |

EC; ethylcellulose
HPMC; hydroxypropyl methylcellulose
TEC; triethyl citrate
*) n = 6

TABLE 2

In vitro dissolution rate: Morphine hydrochloride pellets according to above with a coating of EC:HPMC:TEC = 5.5:3.5:1 at different agitation speed and pH.
Method: USP dissolution apparatus No. II (paddle), 37° C.

| | Dissolution media | | | | |
|---|---|---|---|---|---|
| | pH 6.8 n = 6 | pH 6.8 n = 6 | pH 1.2 n = 3 | pH 4.0 n = 4 | pH 7.6 n = 3 |
| | Agitation speed | | | | |
| Time (hours) | 50 rpm | 100 rpm | 50 rpm | 50 rpm | 50 rpm |
| | percent dissolved morphine hydrochloride | | | | |
| 1 | 8 | 8 | 4 | 5 | 3 |
| 2 | 17 | 16 | 10 | 13 | 10 |
| 3 | 26 | 24 | 16 | 21 | 16 |
| 4 | 34 | 33 | 24 | 28 | 24 |
| 5 | 42 | 40 | 29 | 35 | 30 |
| 6 | 49 | 46 | 35 | 41 | 36 |
| 7 | 55 | 51 | 40 | 47 | 41 |
| 8 | 60 | 57 | 45 | 52 | 47 |
| 10 | 70 | — | 54 | 60 | 55 |
| 24 | 93 | 91 | 82 | 89 | 85 |

TABLE 3

In order to compare the in vitro dissolution rate at different pH, coating film thickness, agitation speed and temperature, the preparation of the following composition was prepared in a comparable manner to the manufacturing procedures above.

Proportion of EC:HPMC:TEC = 8:0.5:1.5

| Active constituent | |
|---|---|
| Morphine hydrochloride | 20 mg |
| Inactive constituents | |
| Lactose | 60 mg |
| Microcrystalline cellulose | 20 mg |
| Water purified* | q.s. |

TABLE 3-continued

In order to compare the in vitro dissolution rate at different pH, coating film thickness, agitation speed and temperature, the preparation of the following composition was prepared in a comparable manner to the manufacturing procedures above.

Proportion of EC:HPMC:TEC = 8:0.5:1.5

| Ethylcellulose | 5.0–7.4 mg |
|---|---|
| Hydroxypropyl methylcellulose | 0.3–0.5 mg |
| Triethyl citrate | 0.9–1.3 mg |
| Ethanol 95%* | q.s. |
| Acetone* | q.s. |
| Water purified* | q.s. |

*Evaporated during the manufacturing process

TABLE 4

In vitro dissolution rate. Morphine hydrochloride CR pellets with different amount of polymers in the coating. Proportions EC:HPMC:TEC = 8:0.5:1.5
Method: USP dissolution apparatus No. II (paddle), 37° C. dissolution medium phosphate buffer, pH = 6.8, agitation speed 50 rpm.

| | Amount of film (% w/w) | | | |
|---|---|---|---|---|
| | 5.8* | 6.9 | 8.6 | 9.2 |
| Time (hours) | percent dissolved morphine hydrochloride, n = 6 | | | |
| 1 | 13 | 8 | 6 | 6 |
| 2 | 30 | 20 | 13 | 11 |
| 3 | 43 | 30 | 21 | 18 |
| 4 | 53 | 38 | 28 | 25 |
| 6 | 68 | 51 | 40 | 35 |
| 8 | 78 | 62 | 51 | 47 |
| 10 | 85 | 71 | 61 | 56 |
| 12 | 90 | 78 | 69 | 63 |
| 15 | 94 | 87 | 78 | 74 |
| 18 | 96 | 92 | 84 | 82 |
| 21 | 98 | 95 | 90 | 89 |
| 24 | 99 | 97 | 93 | 91 |

EC; ethylcellulose
HPMC; hydroxypropyl methylcellulose
TEC; triethyl citrate
*n = 3

TABLE 5

In vitro dissolution tests: Morphine hydrochloride CR according to Table 3 at different pH
Method: USP dissolution apparatus No. II (paddle), 37° C., dissolution agitation speed 50 rpm.

| | Dissolution Medium | | | | |
|---|---|---|---|---|---|
| | pH 1.2 | pH 2.0 | pH 5.8 | pH 6.8 | pH 7.4 |
| Time (hours) | persent dissolved morphine hydrochloride, n = 6 | | | | |
| 1 | 6 | 10 | 10 | 8 | 6 |
| 2 | 15 | 21 | 22 | 20 | 15 |
| 3 | 23 | 30 | 32 | 30 | 22 |
| 4 | 29 | 36 | 40 | 38 | 31 |
| 6 | 41 | 49 | 55 | 51 | 47 |
| 8 | 51 | 60 | 66 | 62 | 59 |
| 10 | 58 | 68 | 75 | 71 | 68 |
| 12 | 65 | 74 | 81 | 78 | 74 |
| 15 | 74 | 82 | 88 | 87 | 85 |
| 18 | 81 | 88 | 93 | 92 | 89 |
| 21 | 85 | 90 | 95 | 95 | 89 |
| 24 | 89 | 94 | 96 | 97 | 92 |

TABLE 6

In vitro dissolution rate. Morphine hydrochloride CR pellets batch according to Table 3 at different agitation speed. Method: USP dissolution apparatus No. II (paddle), 37° C., dissolution medium phosphate buffer, pH 6.8.

| Agitation speed Time (hours) | 40 rpm | 50 rpm | 100 rpm |
|---|---|---|---|
| | percent dissolved morphine hydrochloride, n = 6 | | |
| 1 | 10 | 8 | 12 |
| 2 | 23 | 20 | 25 |
| 3 | 33 | 30 | 35 |
| 4 | 42 | 38 | 44 |
| 6 | 55 | 51 | 58 |
| 8 | 66 | 62 | 67 |
| 10 | 73 | 71 | 75 |
| 12 | 81 | 78 | 80 |
| 15 | 89 | 87 | 88 |
| 18 | 91 | 92 | 90 |
| 21 | 93 | 95 | 92 |
| 24 | 97 | 97 | 96 |

TABLE 7

In vitro dissolution rate. Morphine hydrochloride CR pellets batch according to Table 3 at different temperatures. Method: USP dissolution apparatus No. II (paddle), dissolution medium phosphate buffer, pH 6.8, agitation speed 50 rpm.

| Temperature in dissolution medium Time (hours) | 35° C. | 37° C. | 40° C. |
|---|---|---|---|
| | percent dissolved morphine hydrochloride, n = 6 | | |
| 1 | 12 | 8 | 11 |
| 2 | 23 | 20 | 24 |
| 3 | 33 | 30 | 34 |
| 4 | 41 | 38 | 43 |
| 6 | 52 | 51 | 56 |
| 8 | 65 | 62 | 67 |
| 10 | 70 | 71 | 75 |
| 12 | 79 | 78 | 81 |
| 15 | 85 | 87 | 88 |
| 18 | 91 | 92 | 90 |
| 21 | 94 | 95 | 91 |
| 24 | 93 | 97 | 92 |

As shown in Table 4 it is possible to control the release rate by varying the amount of film coating on the pellets. These experiments show that adequate dissolution rates are obtained and thus makes it possible to fulfil the requirements set on the preparations.

The film components were selected to give release properties that are virtually independent of pH and agitation. By testing the in vitro dissolution rates of the pellets of different batches (see Tables 1–7), the composition of which can be seen in Table 3. By testing the pellets under different conditions (see Tables 2 and 5–7) it is verified that only small variations in dissolution at pH:s appear and that changes in agitation speed and temperature had no significant effect on the release rate.

EXAMPLE 3

Bioavailability study

A single dose, 3-way crossover bioavailability study was performed in 6 healthy individuals. Two prototypes of Morphine controlled release (CR) capsules manufactured in accordance with Examples 1 and 2 of the present invention were studied, see also Tables 8 and 9, below. A morphine oral solution was used as a reference preparation. The subjects received either 30 mg of CR capsule A, 40 mg of CR capsule B or 15 mg of the solution after an overnight fast. Venous blood samples were drawn prior to and during 32 hours after drug administration. Determination of morphine in serum was performed using a specific LC-method with electron capture detection. The area under the serum concentration of morphine vs. the time curve (AUC), the maximum serum concentration, Cmax, the time to reach maximum serum concentration, tmax, the width of the serum concentration vs time curve at half the Cmax concentration ($W_{50}$) and the relative bioavailability of the CR capsules, ($F_{rel}$) was calculated. The results are presented in Table 10 below.

The following preparations were used in the study:

Morphine CR capsules 30 mg formulation A, prepared according to Examples 1 and 2; morphine CR capsules 40 mg formulation B, prepared according to Examples 1 and 2 and morphine oral solution formulation C, 5 mg/ml, as a reference.

TABLE 8

| Constituent | CR capsule A | CR capsule B |
|---|---|---|
| Morphine hydrochloride | 30 mg | 40 mg |
| Lactose | 30 mg | 40 mg |
| Microcrystalline cellulose | 15 mg | 20 mg |
| Water (purified), evaporated in the process | q.s. | q.s. |
| Ethylcellulose (EC) | 1.6–2.4 mg | 3.5–5.3 mg |
| Hydroxypropyl methylcellulose (HPMC) | 1.0–1.6 mg | 2.2–3.4 mg |
| Triethyl citrate (TC) | 03–0.5 mg | 0.6.1.0 mg |
| Ethanol 99.5% (evaporated) | q.s. | q.s. |
| Methyl isobutylketone (evaporated) | q.s. | q.s. |

The in vitro dissolution rates at pH 6.8 are presented in Table 9.

TABLE 9

In vitro dissolution rate of the CR capsules at pH 6.8

| Time (hours) | % dissolved | |
|---|---|---|
| | CR capsule A | CR capsule B |
| 1 | 15 | 8 |
| 2 | 37 | 16 |
| 3 | 56 | 25 |
| 4 | 69 | 34 |
| 5 | — | 42 |
| 6 | 87 | 49 |
| 8 | 95 | 60 |
| 10 | — | 70 |
| 12 | 102 | — |
| 14 | — | 83 |
| 24 | — | 95 |

TABLE 10

Results of a bioavailability study of healthy volunteers:

| Parameter | Capsule A 30 mg | Capsule B 40 mg | Solution 15 mg |
|---|---|---|---|
| AUC (nmol/l*h)[1] | 252.8 ± 115.9 | 304.1 ± 158.6 | 129.4 ± 78.5 |
| $C_{max}$(nmol/l)[1] | 20.9 ± 14.8 | 15.4 ± 9.8 | 34.1 ± 25.8 |
| $t_{max}$(h)[2] | 4.5 (4–5) | 4.5 (4–16) | 0.5 (0.5–0.5) |
| $W_{50}$(h)[2] | 7.73 (5.85–19.4) | >24.3 (14.1–>28.8) | 1.53 (0.65–265) |

TABLE 10-continued

Results of a bioavailability study of healthy volunteers:

| Parameter | Capsule A 30 mg | Capsule B 40 mg | Solution 15 mg |
| --- | --- | --- | --- |
| $F_{rel}$ (%)[3] | 104.1 (83.8–129.4) | 92.0 (68.1–124.4) | — |

[1] = mean ± SD
[2] = median (range)
[3] = mean (90% confidence interval)

The results of the study show very good bioavailability of both CR capsule preparations tested. Capsule A with a dissolution rate profile which makes it suitable for twice daily administration, showed a bioavailability of approximately 100% compared to the solution. Capsule B, with a dissolution rate profile intended for once daily administration showed a slightly lower bioavailability (approx. 90%). However, at the last sampling point (32 hours) the serum concentrations were, in this case, still above half the Cmax concentration and the true bioavailability was thus higher than the calculated figure.

The curve width at half the Cmax concentration $W_{50}$ was about 5 times larger for Capsule A than for the solution. For capsule B $W_{50}$ was at least 15 times larger than for the solution. This, in combination with the excellent bioavailability shows that morphine can be administered once daily in a multiple unit preparation according to the invention and that such a preparation will result in low fluctuations in the serum concentration profiles.

This can be seen in FIG. 1 which shows mean serum concentrations in the six tested individuals versus time for the three preparations A, B, and C. It is obvious from this figure that preparation B, according to the invention, gives almost constant plasma concentrations during 24 hours.

I claims:

1. An oral controlled release pharmaceutical preparation in the form of a multiple unit hard gelatin capsule enclosing particles containing a therapeutically effective amount of a salt of morphine for administration once daily characterized in that it consists of at least 50 particles with a size in the range of 0.2 to 3 mm, each having a core containing a salt of morphine coated with a barrier layer containing at least one water insoluble component selected from the group consisting of ethyl cellulose, copolymers synthesized from acrylic acid esters and methacrylic acid esters, natural waxes, and synthetic waxes, providing a virtually pH-independent drug release within the pH range of 1.0 to 7.0 and in that the serum concentration of morphine obtained is at least 50% of the maximum serum concentration during at least 12 hours after the administration of a single dose of said preparation and providing at least about 80% of the bioavailability of said preparation.

2. A preparation according to claim 1 characterized in that the mean serum concentration of morphine obtained is at least 50% of the maximum serum concentration during at least 18 hours after the administration of a single dose of said preparation.

3. A preparation according to claim 1 characterized in that the drug release through the coating barrier layer is virtually independent of pH within the range 1.0 to 7.0.

4. A preparation according to claim 1 characterized in that the size of the particles is in the range of 0.7 and 1.4 mm.

5. A preparation according to claim 1 characterized in that the coating barrier layer also contains at least one water soluble component selected from the group consisting of hydroxypropylmethyl cellulose, hydroxypropyl cellulose, and copolymers synthesised from acrylic acid esters and methacrylic acid esters, and optionally plasticizers and pigments or both.

6. A preparation according to claim 5 characterized in that the coating barrier layer contains ethyl cellulose, hydroxypropylmethyl cellulose and triethyl citrate as a plasticizer.

7. A preparation according to claim 1 characterized in that the salt of morphine is chosen among morphine hydrochloride, morphine sulphate and morphine salts of organic carboxylic acids.

8. A method for the treatment of severe opioid sensitive pain characterized by administering to a patient a medicament containing the preparation according to claim 1 once daily.

9. A preparation according to claim 2 characterized in that the drug release through the coating barrier layer is substantially independent of pH within the range of 1.0 to 7.0.

10. A method for the treatment of severe opioid sensitive pain characterized by administering to a patient a medicament containing any of the preparations according to claim 2 once daily.

11. A method for the treatment of severe opioid sensitive pain characterized by administering to a patient a medicament containing any of the preparations according to claim 3 once daily.

12. A method for the treatment of severe opioid sensitive pain characterized by administering to a patient a medicament containing any of the preparations according to claim 4 once daily.

13. The preparation of claim 1 containing at least 150 of said particles.

* * * * *